US006352723B1

(12) United States Patent
Lindsey

(10) Patent No.: US 6,352,723 B1
(45) Date of Patent: Mar. 5, 2002

(54) BRAIN-DERIVED ALKALI-SOLUBLE IMMUNOREGULATORY COMPOSITION

(75) Inventor: J. William Lindsey, Houston, TX (US)

(73) Assignee: Research Development Foundation, Carson City, NV (US)

( * ) Notice: Subject to any disclaimer, the term of this patent is extended or adjusted under 35 U.S.C. 154(b) by 0 days.

(21) Appl. No.: 09/494,978

(22) Filed: Jan. 31, 2000

Related U.S. Application Data

(60) Provisional application No. 60/118,930, filed on Feb. 5, 1999.

(51) Int. Cl.[7] .................. A61K 35/30; A61K 35/12; A61K 39/385; A61K 38/16
(52) U.S. Cl. .................. 424/570; 424/193.1; 424/520; 514/2; 514/8; 514/12; 530/350; 530/395
(58) Field of Search .................. 530/350, 395; 514/12, 2, 8; 424/520, 193.1, 570

(56) References Cited

U.S. PATENT DOCUMENTS

| 5,756,300 A | 5/1998 | Seitz |
| 5,762,926 A | 6/1998 | Gage |
| 5,830,670 A | 11/1998 | de la Monte |

OTHER PUBLICATIONS

Wicher et al., Immunol. Commun. 9(5):465–474, 1980.*
Bansil et al., Ann. Neurol., 37(S1):S87–S101, 1995.*
Kahan, B.D., Curr. Opin. Immunol. 4:553–560, 1992.*
Curzio R. Rüegg, et al. Tenascin, and Extracellular Matrix Protein, Exerts Immunomodulatory Activities. *Proc. Natl. Acad. Sci. USA*, vol. 86, pp. 7437–7441 (Oct. 1989).
David N. Irani, et al. Brain Derived Gangliosides Regulate the Cytokine Production and Proliferation of Activated T Cells *Journal of Immunology*, vol. 157, pp. 4333–4340 (1996).
Egar Meinl, et al. Multiple Sclerosis Immunomodulatory Effects of Human Astrocytes on T Cells *Brain*, vol. 117, pp. 1323–1332 (1994).
Helen F. Cserr, et al. Cervical Lymphatics, the Blood–Brian Barrier and the Immunoreactivity of the Brain: A New View *Imm.Today*, vol. 13, pp. 507–512 (1992).
Babita Agrawal, et al. Cancer–Associated MUC1 Mucin Inhibits Human T–Cell Proliferation, Which is Reversible by IL–2 *Nature Medicine*, vol. 4, No. 1, pp. 43–49.

* cited by examiner

Primary Examiner—David Saunders
Assistant Examiner—Amy DeCloux
(74) Attorney, Agent, or Firm—Benjamin Aaron Adler

(57) ABSTRACT

The current invention relates to an active factor present in homogenized brain tissue which inhibits antigen-driven proliferation of lymphocytes in culture, but stimulates proliferation in response to most mitogens. The inhibitory activity can be destroyed by treatment with proteases or neuraminadase. The activity is in the insoluble fraction of the homogenate, but becomes soluble in 0.04 M NaOH. After gel filtration chromatography of the NaOH soluble material, the suppressive activity is in the high molecular weight fraction which elutes in the void volume of the column. This fraction contains protein and carbohydrate. The activity is not affected by neutralizing antibodies against regulatory cytokines, does not depend on Fas or FasL, and is not due to the presence of gangliosides. These data suggest that a brain glycoprotein which is either membrane-bound or part of the extracellular matrix has powerful immune regulatory effects in culture.

6 Claims, 7 Drawing Sheets

BRAIN-DERIVED ALKALI-SOLUBLE IMMUNOREGULATORY COMPOSITION

CROSS-REFERENCE TO RELATED APPLICATION

This application claims benefit of U.S. provisional application Ser. No. 60/118,930, filed Feb. 5, 1999, now abandoned.

BACKGROUND OF THE INVENTION

1. Field of the Invention

The present invention relates generally to the fields of immunology and neurobiology and also relates generally to the study of multiple sclerosis. More specifically, the present invention relates to an active factor present in homogenized brain tissue which inhibits antigen-driven proliferation of lymphocytes in culture, but stimulates proliferation in response to most mitogens.

2. Description of the Related Art

The brain has long been considered an immune-privileged site, along with the eye, the gravid uterus, and the testis [1, 2]. Immune privilege is probably due to active immune regulation in the privileged site rather than isolation of the privileged site from the immune system and probably results from the combined effects of multiple regulatory mechanisms. Mechanisms which contribute to immune regulation in the eye include soluble immunosuppressive factors and possibly the constitutive expression of Fas ligand [3, 4]. These mechanisms may also be operative in the brain [5, 6]. Gangliosides may also regulate immune responses in the brain [7]. There are probably several other mechanisms as well.

One possible immunoregulatory agent which has received little attention is the parenchymal microenvironment. The effector phase of immune responses occurs at least in part in the tissues, and the effector cells are in intimate contact with the extracellular matrix and the extracellular surfaces of parenchymal cells. It is reasonable to expect that molecules present in the extracellular environment could convey regulatory signals to immune effector cells through interaction of the molecules present in the extracellular space with specific receptors on immune cells. A normal extracellular environment might inhibit immune responses, while an extracellular environment altered by the effects of infectious organisms might promote immune responses [8]. The extracellular environment in immune privileged sites such as the brain might have unique regulatory effects.

The prior art is deficient in the lack of the identification of the factors responsible for the inhibition of immune function in the brain. The present invention fulfills this longstanding need and desire in the art.

SUMMARY OF THE INVENTION

The current invention comprises a brain homogenate which inhibits the proliferation of lymphocytes resulting from stimulation with antigens such as chicken ovalbumin (OVA) and the purified protein derivative (PPD) of *Mycobacterium tuberculosis*. This inhibition appears to involve the blocking of the stimulatory effect of IL-2 on the proliferation of the antigen-stimulate lymphocytes The brain homogenate can also be used to affect mitogen stimulated lymphocyte proliferation. With most mitogens, including concanavalin A (ConA), lipopolysaccharide (LPS), and anti-CD3 antibody, the brain homogenate enhances the mitogen stimulated proliferation of the lymphocytes. One exception is the mitogen mixture ionomycin with phorbol 12-myristate 13-acetate (PMA), where the brain homogenate suppresses the mitogen induced proliferation of the lymphocytes The current invention also comprises an active factor present in the brain homogenate which has been demonstrated to contain most of activity of the homogenate with respect to the lymphocyte proliferation. The active factor is part of a particulate complex which forms a sediment at 14,000 g and is heat and formalin stable. The active factor contains terminal sialic acid residues and is inactivated by digestion with trypsin or proteinase K but not with hyaluronidase.

The active factor can be partially isolated from the brain homogenate by centrifugation, solubilization in alkali, and partial purification on a SUPEROSE™ 6HR 10/30 sepharose gel filtration column equilibrated with 0.04 N NaOH, where the factor elutes in the void volume.

The present invention also comprises a pharmaceutical composition which can be used to treat pathophysiological states characterized by undesired activity of the immune system. Possible uses include the treatment of various autoimmune diseases including multiple sclerosis.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

Cells were incubated with no antigen, chicken ovalbumin, chicken ovalbumin plus brain homogenate, chicken ovalbumin plus the NaOH supernatant, and chicken ovalbumin plus the NaOH sediment. After suspension in NaOH, most of the activity dissolves and remains in the supernatant. Some activity remains in the sediment.

Figure 6A:
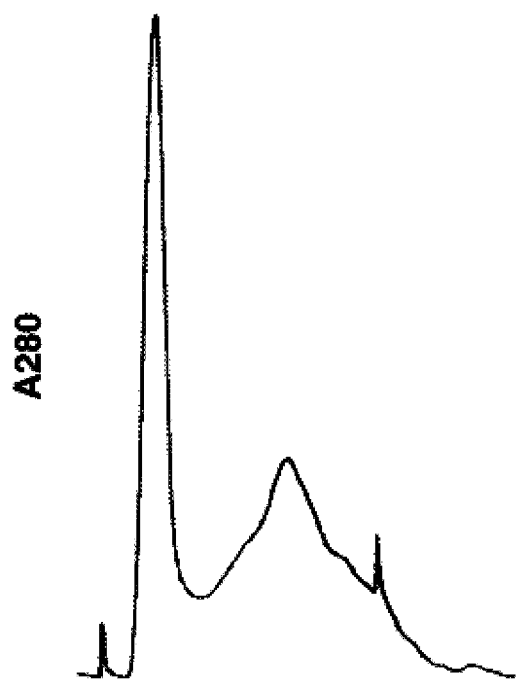
Figure 6B:
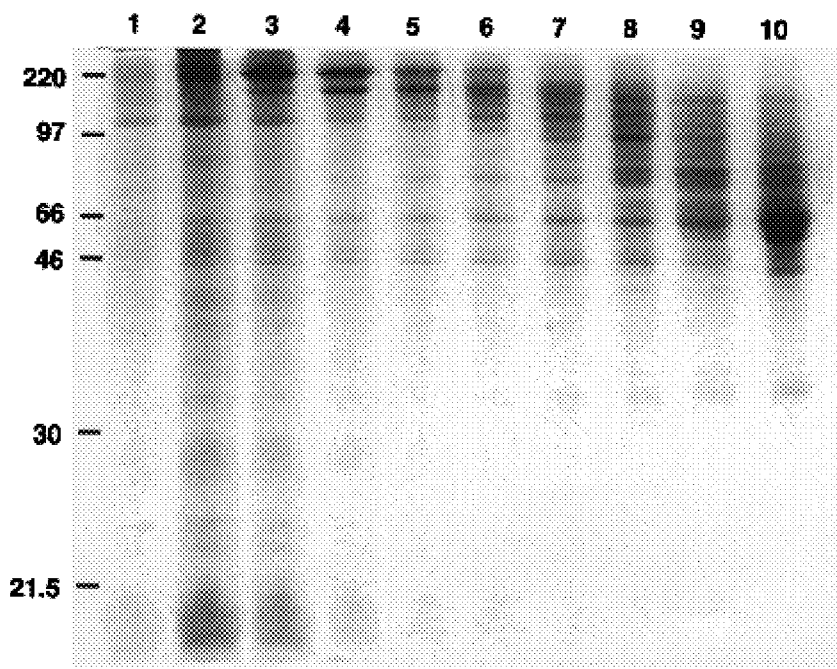
Figure 7:
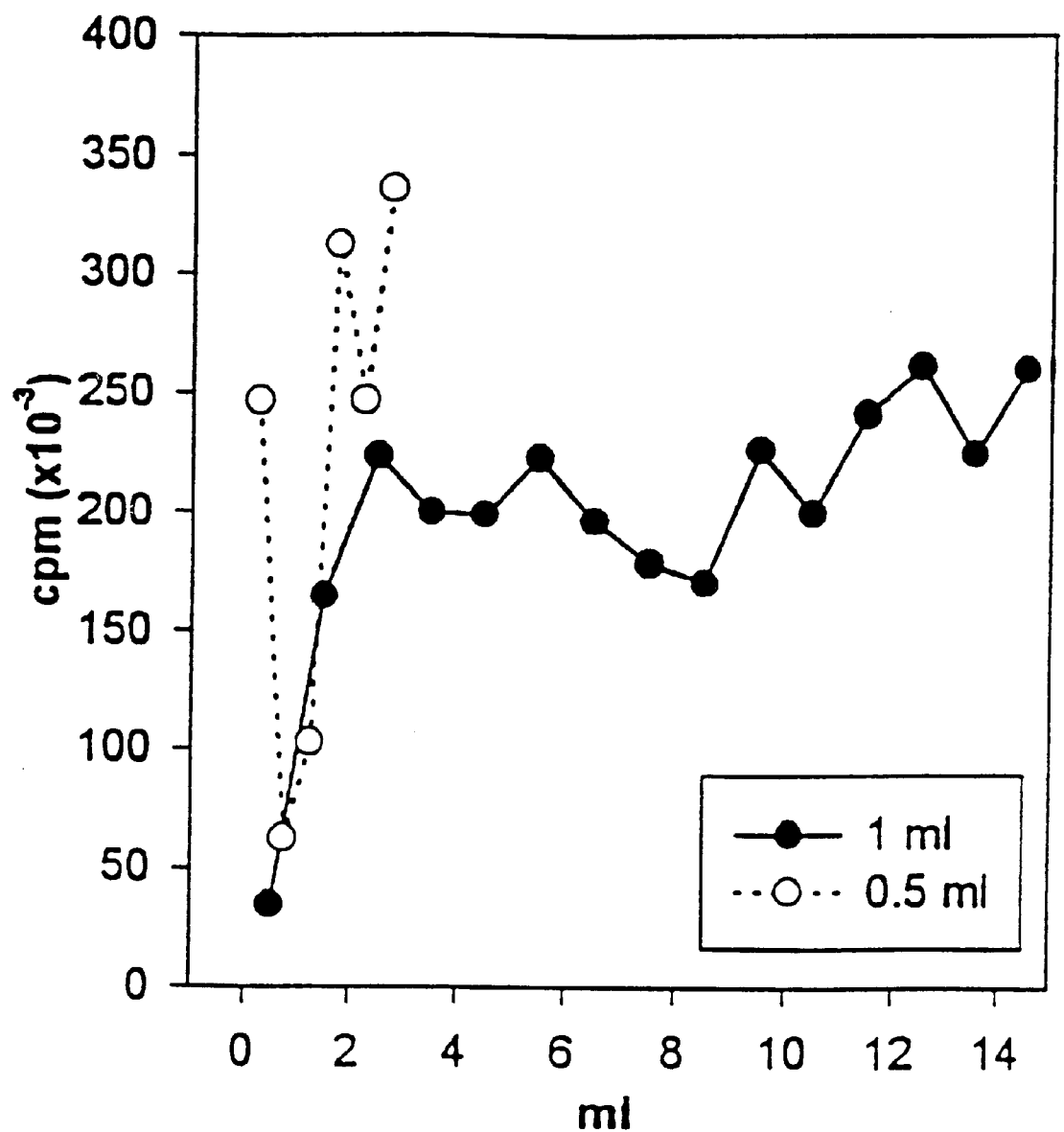

FIGS. 6A and 6B illustrate column purification of the suppressive factor. FIG. 6A shows the UV absorbance at 280 nm of column effluent. The suppressive activity is in the first, high-molecular weight peak which eluted over 4 minutes in a total volume of about 2 ml. The spikes before the first peak and on the tail of the second peak is are artifacts. FIG. 6B shows SDS-PAGE of ten sequential 0.5 ml fractions covering the first peak and early part of the second peak. The numbers on the left indicate approximate molecular weight in kilodaltons. In this particular example, the majority of the activity is in fraction 2, FIG. 7 shows the effect of column fractions on proliferation. Results of two separate experiments are shown. One ml or 0.5 ml fractions were collected and tested for their effect on chicken ovalbumin induced proliferation. Proliferation for each fraction is plotted at the midpoint of that fraction, e.g. the first one ml fraction is plotted at 0.5 ml, and the first 0.5 ml fraction is plotted at 0.25 ml. Abscissa is ml of column effluent, starting with the onset of the first UV absorbent peak. The peak suppressive activity is in the first 1 ml fraction and the second and third 0.5 ml fractions.

DETAILED DESCRIPTION OF THE INVENTION

The current invention is directed to a brain homogenate which inhibits the proliferation of antigen-stimulated lymphocytes but increases the proliferation of most mitogen-stimulated lymphocytes. Specifically, stimulation of lymphocyte proliferation by chicken ovalbumin (OVA) and the purified protein derivative (PPD) of *Mycobacterium tuberculosis* was demonstrated to be inhibited by the addition of the brain homogenate. This may occur by blocking the stimulatory effects of IL-2 on the proliferation of the antigen-stimulated lymphocytes.

Lymphocyte proliferation resulting from stimulation with the mitogens concanavalin A (ConA), lipopolysaccharide (LPS), and anti-CD3 antibody was enhanced by the addition of the brain homogenate. One exception to the general rule that the brain homogenate stimulates mitogen-induced lymphocyte proliferation is the mitogenic mixture of ionomycin with phorbol 12-myristate 13-acetate (PMA) in which lymphocyte proliferation was suppressed by the brain homogenate.

In another embodiment of the current invention, most of the activity of the brain homogenate can be linked to an active factor which is present in a particulate complex which can be sedimented by centrifugation at 14,000 g. The active factor is heat stable and is not sensitive to formalin treatment. It has been demonstrated to have terminal sialic acid residues and is inactivated by protease digestion trypsin or proteinase K but not with hyaluronidase.

The active factor can be partially purified by centrifugation, solubilization of the resulting pellet in alkali, and application to a SUPEROSE™ 6HR 10/30 sepharose gel filtration column where it elutes into the void volume.

Another embodiment of the present invention is a pharmaceutical composition containing the active factor to be used for the treatment of a pathophysiological state characterized by undesired proliferation of antigen-stimulated lymphocytes. Autoimmune diseases, e.g., multiple sclerosis, rheumatoid arthritis, Diabetes mellitis, systemic lupus erythematosus, etc, are possible targets of such a pharmaceutical composition.

The following examples are given for the purpose of illustrating various embodiments of the invention and are not meant to limit the present invention in any fashion.

EXAMPLE 1

Brain Homogenate

Naïve mice were sacrificed by $CO_2$ narcosis and perfused with 10 cc of normal saline. The brain was removed and homogenized in 10 mM HEPES in a Dounce tissue homogenizer at a concentration of 125 mg wet tissue per ml. Before use in tissue culture, the homogenate was irradiated with 2000 rads in a cesium irradiator to ensure sterility. Brain homogenate was usually used in tissue culture at a concentration of 2.5 mg wet tissue/ml.

EXAMPLE 2

Isolation of Stimulated Lymphocytes

ICR female mice weighing 21 to 24 grams were obtained from Harlan Sprague-Dawley (Houston, Tex.), and 6 week old female DBA/2J, C3H.MRL-$Fas^{lpr}$ and C3H/HeJ-$Fas^{gld}$ mice were obtained from Jackson Laboratories (Bar Harbor, Me.). To induce antigen specific proliferative responses, animals were injected subcutaneously in both flanks and over the scapula with a total of 0.2 cc of an emulsion containing 2 mg/ml chicken ovalbumin (OVA, Sigma, St. Louis, Mo.) and 2 mg/ml lyophilized Mycobacterium tuberculosis (MTb, Difco, Detroit, Mich.) in equal parts of phosphate buffered saline (PBS) and incomplete Freund's adjuvant (IFA, Difco). Ten to 30 days later, the mice were euthanized by $CO_2$ narcosis and axillary, inguinal, and para-aortic lymph nodes were removed. A single cell suspension was prepared by grinding the lymph nodes between glass slides, and the cells were washed twice in Hank's balanced salt solution.

EXAMPLE 3

Cell Culture of Stimulated Lymphocytes

Cells were cultured at $2 \times 10^5$/well in triplicate in 96 well plates in RPMI 1640 medium supplemented with 5% fetal calf serum, 2 mM glutamine, 100 U/ml penicillin, 0.1 mg/ml streptomycin, and $5 \times 10^{-5}$ M 2-mercaptoethanol (all from Gibco, Grand Island, N.Y.). The total volume per well was 200 microliters, and the cells were incubated at 37° C. with 5% CO2.

EXAMPLE 4

Proliferation Assay for Stimulated Lymphocytes

The plates were pulsed with 1 microcurie/well of tritiated thymidine after 48 hours and harvested onto fiberglass filter paper 18 hours later using a semi-automated cell harvester. The amount of incorporated thymidine was counted on a Beckman LS-1801 scintillation counter.

Because of variations in amount of stimulation, % suppression is used to combine data from different animals. The percent suppression was calculated as:

$$\% \text{ Suppression} = 100 \times (\text{cpmst} - \text{cpmst+su})/(\text{cpmst} - \text{cpmba})$$

where cpmba is the background counts per minute, cpmst is the counts per minute with the stimulating antigen, and cpmst+su is the counts per minute with the stimulating or suppressing antigen. In all cases where the effects of different suppressing antigens are compared, the two suppressing antigens were tested in the same group of animals. Values are expressed as the mean standard deviation of at least three independent experiments.

In some cases, the results are represented as the stimulation index (SI) which was calculated as: SI=cpmst/cpmba, where cpmba is the background counts per minute, and cpmst is the counts per minute with the stimulating antigen.

EXAMPLE 5
Effect of Brain Homogenate on Lymphocyte Proliferation

Figure 1:
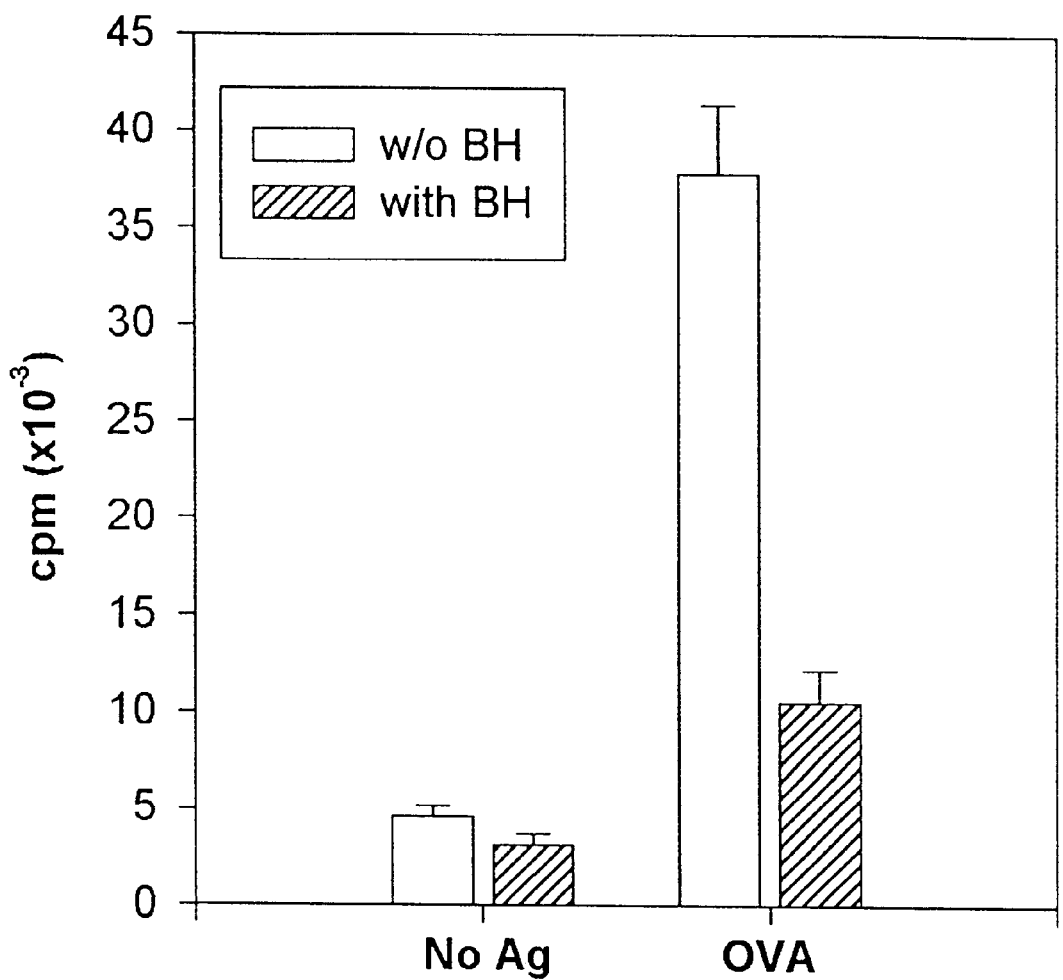
FIG. 1 shows an example of the effect of brain homogenate on proliferation to ovalbumin and background response. Cells were cultured with no antigen or ovalbumin, both with and without brain homogenate (BH). Proliferation is given as cpm in thousands. Error bars indicate standard deviation for triplicate wells. The addition of brain homogenate suppressed antigen-driven proliferation by 82%.

Cells from animals immunized with chicken ovalbumin in Freund's adjuvant were cultured with no antigen, 500 µg/ml chicken ovalbumin, and 500 µg/ml chicken ovalbumin plus brain homogenate. Brain homogenate at a concentration of 2.5 mg/ml consistently inhibited antigen-driven proliferation to chicken ovalbumin by 70 to 100% (FIG. 1). Background proliferation is relatively high in ICR mice (typically around 4000 cpm), and the brain homogenate suppressed the background proliferation about 60%. The effect of brain homogenate was less at lower concentrations, with the % suppression decreasing as an approximately linear function of the log of the homogenate concentration. Suppression was 86±11% at 2.5 mg/ml, 56±14% at 0.75 mg/ml, and 35±17% at 0.25 mg/ml (n=5).

EXAMPLE 6
Preincubation of OVA with Brain Homogenate

Suppression was not due to absorption, binding, or degradation of chicken ovalbumin by the brain homogenate. Chicken ovalbumin which was incubated with homogenate and then centrifuged and passed through a 0.2µ filter to remove the homogenate stimulated as well as chicken ovalbumin incubated without brain homogenate (SI 4.8±1.8 for chicken ovalbumin incubated with brain homogenate vs. 4.1±0.9 for chicken ovalbumin incubated alone, n=4).

EXAMPLE 7
The Effect of Brain Homogenate on Cell Proliferation is not Due to Toxicity Suppression was not due to a toxic effect of the brain homogenate, although the brain homogenate did modestly reduce the number of viable cells. The brain homogenate was tested for direct toxicity to cells by incubating lymph node cells in triplicate wells with or without brain homogenate at 2.5 mg/ml. After two days, the number of viable cells in each well was counted in a hemacytometer using trypan blue exclusion as the criteria for viability. When cells were counted with a hemacytometer after two days of culture, 52±24% of cells cultured with no antigen were still viable, while 36±11% of cells cultured with brain homogenate were viable (n=6). The difference in numbers of viable cells may reflect the effect of the brain homogenate on the high background proliferation in the ICR strain. Similar experiments with DBA/2 mice confirmed the minimal effect of brain homogenate on cell survival as 34±26% of cells cultured with no antigen were viable while 29±22% of cells cultured with brain homogenate were viable (n=4).

EXAMPLE 8
Effect of Brain Homogenate on Proliferation Induced by Other Antigens and Mitogens The effect of brain homogenate was tested using other antigens or mitogens. Chicken ovalbumin at 500 µg/ml and purified protein derivative of *Mycobacterium tuberculosis* (PPD, Parke-Davis, Rochester, Mich.) at 25 µg/ml were used as stimulating antigens. Mitogens used were Concanavalin A (ConA, Sigma) at 2.5 µg/ml, Lipopolysaccharide (LPS) from *E. coli* (Sigma) at 10 µg/ml, anti-CD3 antibody (Southern Biotechnology, Birmingham, Ala.) at 0.1 or 1.0 µg/ml, and ionomycin at 100 ng/ml with 1 ng/ml phorbol 12-myristate 13 acetate (PMA) (Sigma).

Figure 2:
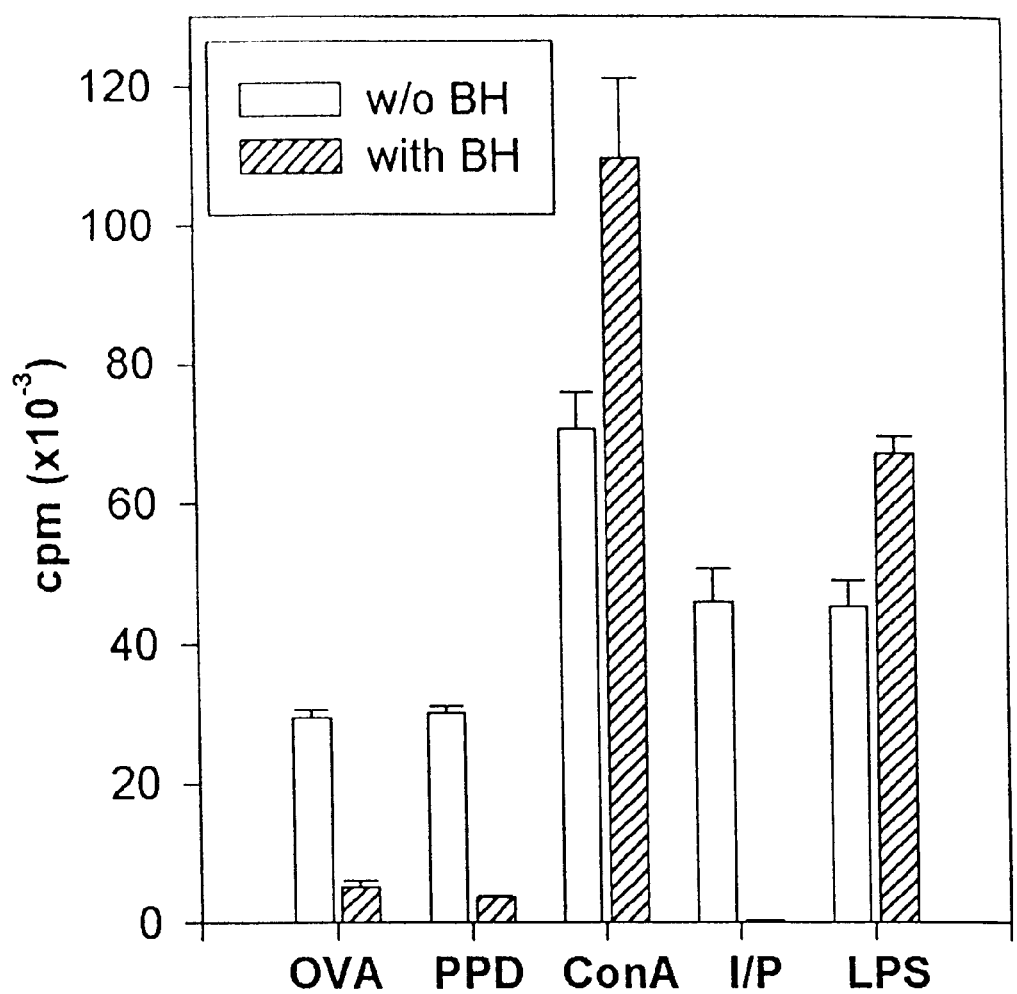
FIG. 2 shows that the brain homogenate suppresses antigen-driven proliferation but increases proliferation to some mitogens. Representative results from a single animal are shown. Cells were cultured with various antigens or mitogens without and with brain homogenate. Background proliferation was $2.1 \times 10^3$ cpm. Abbreviations and error bars as in FIG. 1. I/P is ionomycin/PMA.
Figure 3:
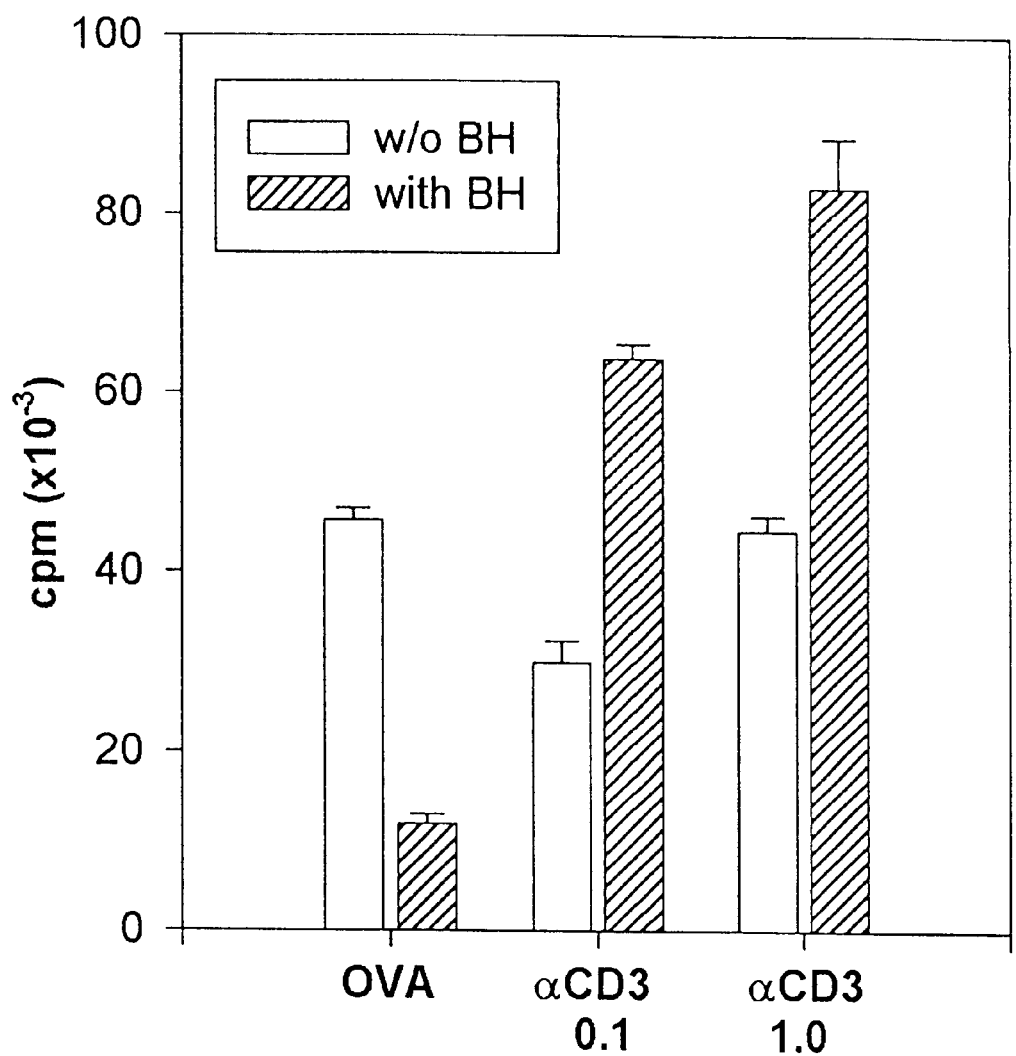
FIG. 3 shows that the brain homogenate suppresses proliferation to chicken ovalbumin but not to anti-CD3 antibody. Representative results from a single animal are shown. Background proliferation was $5.0 \times 10^3$ cpm. Anti-CD3 antibody was at 0.1 or 1.0 µg/ml.

Brain homogenate suppressed proliferation to the purified protein derivative of *Mycobacterium tuberculosis*, but did not suppress proliferation induced by the mitogens ConA, LPS, or anti-CD3 antibodies (FIGS. 2 and 3, Tables 1 and 2). For these three mitogens, the presence of brain homogenate usually increased the proliferation rather than suppressing it. Proliferation to mitogens was usually much greater than proliferation to antigens, but brain homogenate still caused increased proliferation in response to the lower concentration of anti-CD3 antibody which had a stimulation index similar to that for chicken ovalbumin. Curiously, proliferation to ionomycin/PMA was profoundly suppressed. This was not due simply to absorption of the mitogen by the brain homogenate, since ionomycin/PMA which was incubated with brain homogenate for up to 4 hours retained its ability to stimulate proliferation after the brain homogenate was removed by centrifugation.

TABLE 1

Effect of Brain Homogenate on Proliferation to Antigens and Mitogens

| Stimulating Antigen or Mitogen | SI | % Suppression with BH |
| --- | --- | --- |
| OVA | 8.8 ± 5.8 | 84 ± 7 |
| PPD | 12.3 ± 8.4 | 78 ± 15 |
| ConA | 31.2 ± 32.7 | −76 ± 77 |
| Ionomycin/PMA | 23.6 ± 11.2 | 104 ± 2 |
| LPS | 16.8 ± 16.5 | −88 ± 69 | n = 6, background = 4600 ± 3100 cpm

TABLE 2

Effect of Brain Homogenate on Proliferation to OVA and Anti-CD3 Antibody

| Stimulating Antigen or Mitogen | SI | % Suppression with BH |
| --- | --- | --- |
| OVA | 7.9 ± 4.2 | 94 ± 17 |
| Anti-CD3 0.1 µg/ml | 7.1 ± 3.3 | −71 ± 67 |
| Anti-CD3 1.0 µg/ml | 10.8 ± 7.5 | −53 ± 33 | n = 6, background = 4100 ± 2000 cpm

EXAMPLE 9
The Suppressive Factor is Particulate and Heat Stable

Several investigations were performed to further define the nature of the suppressive activity. Homogenate was separated into supernatant and sediment by centrifugation at 14,000 g for 5 minutes. Sediment was resuspended in the original volume by pipetting. After centrifugation, the majority of the activity was in the sediment. The % suppression from the unfractionated homogenate was 100±10, while the % suppression in the sediment was 91±9, and the % suppression in the supernatant was 10±15 (n=6). Delaying the addition of the brain homogenate to the culture by 24 hours decreased the % suppression from 90±10 to 68±10 (n=5).

The effects of formalin and heat on the brain homogenate were also assayed. Formalin treated homogenate was prepared by resuspending the sediment in 10% formalin, and incubating at room temperature for 1 hour. Formalin was washed out by three cycles of centrifugation at 14,000 g for 5 minutes followed by resuspension in PBS. Heat inactivated homogenate was prepared by heating to 95° C. for 10 minutes. Exposure to formalin or to heat had no significant effect on the activity.

EXAMPLE 10

Gangliosides

The possibility that gangliosides were the active factor was considered. This possibility was tested directly by comparing the effects of brain homogenate, mouse gangliosides, and bovine gangliosides on proliferative responses in culture.

Bovine gangliosides type IV were obtained from Sigma. Literature values for the expected concentration of gangliosides in mouse brain range from 20 to 3.3 mg per gram of wet tissue [9–11]. If the higher value is used, then 2.5 mg/ml of brain homogenate corresponds to 8.25 µg gangliosides/ml. The bovine gangliosides were used at this concentration and at 3 times and 10 times this concentration. The value of 3.3 mg/ml is for mouse cortex and is probably an overestimate of the amount present in whole brain homogenate since concentrations of gangliosides are lower in white matter.

Gangliosides from mouse brain were isolated by extraction of the crude homogenate with chloroform:methanol followed by partitioning into 0.1 M KCl as described [12]. After lyophilization, the extracted gangliosides were redissolved in PBS, and the volume adjusted to equal the original volume of brain homogenate used in the extraction procedure. The presence of gangliosides was confirmed by high performance thin layer chromatography (HPTLC) on silica gel plates and visualization with the resorcinol reagent.

Gangliosides had only a minimal effect on proliferation at concentrations corresponding to the amount present in 2.5 mg/ml of brain homogenate. Gangliosides had an effect equivalent to brain homogenate only when used at 10 times the equivalent concentration (Table 3). The dose response relation for gangliosides found in these experiments is similar to that previously reported [7].

TABLE 3

Comparison of brain homogenate and gangliosides

| | | % Suppression | |
|---|---|---|---|
| Concentration | BH | Mouse ganglio. | Bovine ganglio. |
| 1× | 102 ± 15 | −5 ± 8 | 12 ± 9 |
| 3× | | 27 ± 7 | 56 ± 27 |
| 10× | | | 83 ± 32 | n = 4, SI with OVA 5.5 ± 2.2, background 4000 ± 1400 cpm

EXAMPLE 11

Effects of Enzymatic Digestion

To further define the nature of the suppressive activity, the homogenate was treated with different enzymes. Brain homogenate in 100 µl aliquots was centrifuged and resuspended in the appropriate buffer for the enzyme. Enzyme was added at different concentrations, and each experiment included an aliquot without enzyme to serve as a control for possible effects of incubation in buffer alone. All aliquots were incubated for 4 hours at 37° C., and then washed three times by serial centrifugation and resuspension in PBS to remove the enzyme and any soluble digested fragments. After the last wash, the sediment was resuspended in the original volume of PBS for use in tissue culture.

Neuraminidase Type II from Vibrio cholera was used at 0.01 U or 0.05 U per aliquot in 80 mM sodium acetate 80 at pH 5.5. The first supernatant after neuraminadase treatment was stored for determination of sialic acid concentration using the ferric chloride-orcinol method [13]. The results of the neuraminidase treatment are summarized in Table 4 and in FIG. 4.

Neuraminidase removes terminal sialic acid residues from glycoproteins or glycolipids and is most active at pH 5.5. Incubation of the brain homogenate in the enzyme buffer with no enzyme resulted in some loss of activity. The addition of enzyme resulted in further loss of activity. With large amounts of enzyme (0.05 U/100 µl), the remaining homogenate became stimulatory with a % suppression of −131±41 (n=4). The ferric chloride-orcinol assay [13] confirmed that the enzyme released sialic acid into the supernatant. These results were obtained with a neuraminadase purified from Vibrio cholera which may also contain protease activity, but there was no evidence of proteolytic degradation on SDS PAGE.

Figure 4:
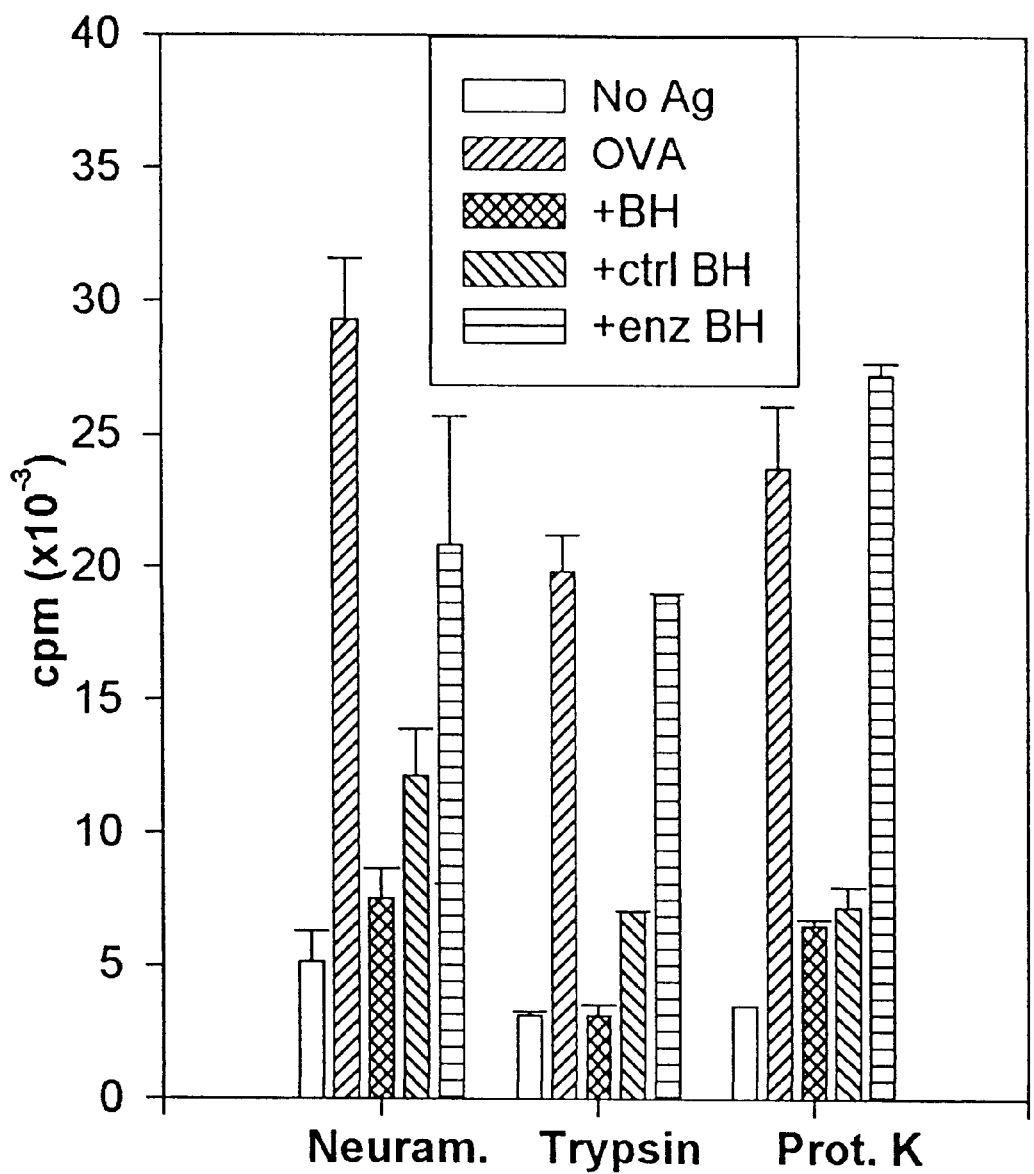
FIG. 4 shows that neuraminadase and proteases destroy the suppressive activity. Results from individual animals are shown. Cells were incubated with no antigen, chicken ovalbumin alone, chicken ovalbumin plus brain homogenate, chicken ovalbumin plus brain homogenate which had been incubated in the enzyme buffer without enzyme, and brain homogenate which had been exposed to active enzyme. Neuram. is neuraminadase. Prot. K is proteinase K. Exposure to the enzymes destroyed the activity. The acidic neuraminadase buffer also removed some activity.

Similar destruction of the activity was obtained with proteases (Table 4, FIG. 4). Trypsin from bovine pancreas was used at 0.5 mg per aliquot in 0.1 M ammonium bicarbonate. Proteinase K (0.1 mg) and hyaluronidase from sheep testes (1 mg) were both used in PBS. Incubation of the crude homogenate with trypsin destroyed the suppressive activity. Proteinase K also destroyed the suppressive activity and the remaining sediment stimulated proliferation rather than suppressing it. In contrast, hyaluronidase digestion had only a small effect.

TABLE 4

Effects of enzyme digestion

| | | % Suppression | | | |
|---|---|---|---|---|---|
| Enzyme | SI | BH | Buffer Control BH | Enzyme Treated BH | n |
| Neuraminidase 0.01 U | 4.9 ± 1.1 | 97 ± 16 | 66 ± 16 | 23 ± 14 | 6 |
| Trypsin 0.5 mg | 6.6 ± 2.0 | 87 ± 14 | 79 ± 17 | −1 ± 13 | 6 |
| Proteinase K 0.1 mg | 5.4 ± 2.0 | 89 ± 4 | 85 ± 5 | −48 ± 45 | 5 |
| Hyaluronidase 1 mg | 4.8 ± 1.1 | 101 ± 9 | 105 ± 5 | 90 ± 15 | 9 |

"buffer control" is brain homogenate incubated in the enzyme buffer without enzyme

EXAMPLE 12

Alkaline Solubilization

The active factor was insoluble at neutral pH, but became soluble in alkali. Brain homogenate was divided into 0.4 ml aliquots, centrifuged and resuspended in 0.4 ml PBS with 10 mM magnesium chloride, 100 U DNAse, 80 µg RNAse, and protease inhibitors, and incubated for 45 minutes at 37° C. The aliquots were then washed three times with sterile water and brought back up in 1 ml of water after the final wash. Sodium hydroxide was added to a final concentration of 0.04 M, and the aliquots were combined, vortexed briefly, and centrifuged at 40,000 g for 30 minutes. The supernatant was collected by pipetting, and the pellet was washed once with 0.04 M sodium hydroxide to remove residual supernatant and then resuspended in the original volume of PBS. Before use in tissue culture, the supernatant was neutralized with the addition of 10×PBS and 1 M HCl. Upon neutralization, a cloudy precipitate formed in the previously clear supernatant. This precipitate could be separated from the supernatant by centrifugation for 5 minutes at 14,000 g, and was subjected to digestion with neuraminidase or proteinase K as described above.

Figure 5:
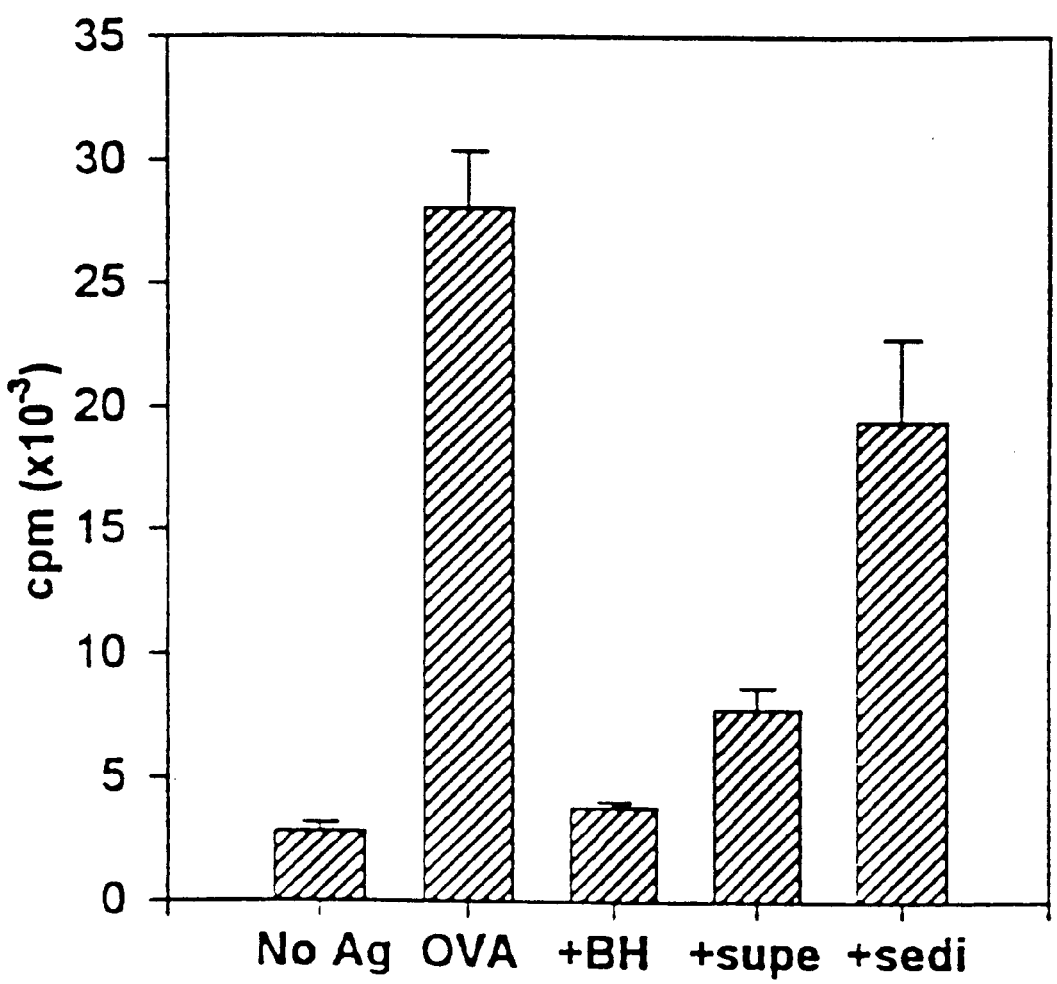
FIG. 5 shows that alkali solubilizes the suppressive activity. Representative results from a single animal are shown.

Suspension of the sediment from the crude homogenate in 0.04 M NaOH followed by centrifugation at 40,000 g resulted in a clear supernatant and a small pellet. Most of the activity remained in the supernatant (representative example in FIG. 5). The suppression with the DNAse treated homogenate was 92±8%, while suppression with the NaOH supernatant was 78±7% and the NaOH sediment suppressed 23±25% (n=14).

On SDS-PAGE, most of the proteins were in the NaOH soluble fraction with minimal proteins visible in the pellet. Passing the NaOH supernatant through a 0.2μ filter caused rapid clogging of the filter and a modest loss of activity from 71±12% to 64±11% suppression (n=7). When the NaOH supernatant was brought back to neutral pH, a fine precipitate formed which formed a sediment upon brief centrifugation. The % suppression from the neutralized NaOH supernatant was 75±5, while the suppression from the neutralized sediment was 62±11, and the neutralized supernatant was 13±8 (n=4).

EXAMPLE 13
Gel Filtration

To further characterize the activity, the filtered NaOH supernatant was fractionated on a gel filtration column. The NaOH supernatant was filtered through a 0.2μ filter and then 0.5 ml was loaded onto a SUPEROSE™ 6HR 10/30 sepharose gel filtration column equilibrated in 0.04 M NaOH and eluted at a flow rate of 30 ml/hour on a fast protein liquid chromatography system (Pharmacia, Uppsala, Sweden). The UV absorbence of the column outflow was monitored at 280 nm, and fractions, varying in size from 0.5 to 2.0 ml in different experiments, were collected, starting with the first absorbence peak. The UV absorbent material eluted in about 14 ml. For tissue culture, aliquots taken from the column fractions were neutralized by adding appropriate amounts of 1 M HCl, 10×RPMI, and fetal calf serum and used at 25, 50 or 100 μl/well.

Two major UV absorbent peaks were present (FIG. 6). An initial large peak was followed by a broader second major peak formed by the overlapping peaks of individual proteins. On SDS-PAGE, the early peak contained proteins with molecular weight greater than 200 kD and some lower molecular weight proteins which must have been present as part of a macromolecular complex. The second peak contained proteins of molecular weight less than 200 kD. In initial experiments, one ml or two ml fractions were collected covering both peaks, and it was found that the suppressive activity was in the first peak (FIG. 7). In subsequent experiments, six 0.5 ml fractions were collected which covered the first peak. The suppressive activity was primarily in the second and third fractions.

EXAMPLE 14
Characterization of the First Peak

In addition to the proteins, the high molecular weight, base-soluble fraction could contain proteoglycans and glycosaminoglycans. It could also include DNA, even though the samples had been treated with DNAse before extraction with base. Concentrations of DNA, protein, and carbohydrate in the column fractions were determined using spectrophotometric or fluorometric assays. Concentration of DNA was determined with Hoechst 33258 fluorometric assay [14]. Protein concentration was determined using the Bradford assay [15]. Hexosamine concentration was measured using the 3-methyl-2-benzothiazolinone hydrazone hydrochloride method, uronic acids were quantitated using meta-hydroxybiphenyl method, and sialic acids were measured using the ferric chloride-orcinol method [13]. All reagents for these assays were obtained from Sigma.

Assay of fractions containing the entire first peak demonstrated the presence of protein and carbohydrates and low amounts of DNA (Table 5). Analysis of 0.5 ml fractions demonstrated that protein and hexosamine concentrations were highest in the second and third fractions, which correlated with the observed % suppression in proliferation assays.

TABLE 5

Composition of the Active Fraction

|  | Concentration (μg/ml) |
|---|---|
| Protein | 46 |
| Hexosamine | 8.6 |
| Uronic acid | 3.2 |
| DNA | 1.7 |

Representative example of five independent experiments

EXAMPLE 15
Mechanism

The possibility that the anti-proliferative effect of brain homogenate might be mediated through known anti-inflammatory cytokines or through Fas ligand was explored. Addition of 10 mg/ml of antibodies against TGF-β, IL-4, and IL-10 (Neutralizing antibodies obtained from R&D Systems, Minnesota, Minn.) increased the proliferation to OVA but did not block the inhibitory effect of brain homogenate. The % suppression in the presence of antibodies was 93±10% compared to 101±8 without antibodies (SI=5.6±0.6 without antibodies, 7.6±1.0 with antibodies, n=4). Similarly, Fas and Fas ligand did not appear to play a role (Table 6). Brain homogenate from FasL deficient mice had an inhibitory effect equivalent to brain homogenate from wild type mice, and the proliferation of Fas deficient lymphocytes was inhibited to a similar degree as wild-type lymphocytes.

TABLE 6

Comparison of lymphocytes and brain homogenate from wild type, FasL deficient and Fas deficient mice

|  |  | % Suppression | | | |
|---|---|---|---|---|---|
| Lymphocytes | SI | wt BH | FasL-BH | Fas-BH | n |
| wt | 8.3 ± 4.7 | 107 ± 5 | 99 ± 13 | 95 ± 10 | 3 |
| FasL- | 7.7 ± 0.6 | 94 ± 8 | 97 ± 8 | 91 ± 6 | 2 |
| Fas- | 6.5 ± 1.5 | 99 ± 9 | 97 ± 5 | 89 ± 7 | 3 |

"wt" = wild type DBA/2J, BH = brain homogenate

EXAMPLE 16
Effects of Brain Homogenate on IL-2 Pathway

Another possible mechanism for the action of the brain homogenate is by blocking the effects of IL-2. Brain homogenate markedly suppressed the effects of IL-2. Addition of 10 ng/ml IL-2 to the culture media increased background proliferation and antigen-driven proliferation. However, brain homogenate almost completely blocked this increase in proliferation. Brain homogenate suppressed the proliferation to IL-2 by 83±12% (n=6, SI with IL-2=8.0±2.8). Brain homogenate could conceivably affect IL-2 secretion also, but attempts to measure the effect of brain homogenate on IL-2 secretion using ELISA were inconclusive because of the relatively small increase in IL-2 secretion seen with OVA (data not shown).

Interpretation of Results

These experiments demonstrate that normal brain tissue contains a factor which profoundly inhibits lymphocyte proliferation through a mechanism which includes blocking the stimulatory effects of IL-2. The effects of enzymatic digestion and the results of the chemical assays of the column fractions suggest that the primary active factor is a glycoprotein or proteoglycan. This factor is part of a macromolecular assembly as indicated by the fact that it is insoluble in its native form, becomes soluble in alkali, and becomes insoluble again at neutral pH. It could either be a component of the extracellular matrix or a membrane bound glycoprotein. The activity could also be due to the combined effects of a protein and a non-protein glucoconjugate (e.g. A ganglioside, glycolipid, or small glycoprotein) as well. This activity is distinct from potential immunoregulatory factors present in brain previously described, since the experiments described above suggest that it is not due to gangliosides, FasL, or regulatory cytokines. The fact that the brain homogenate inhibits proliferation to antigens but stimulates proliferation to most mitogens is intriguing. An explanation will require a better understanding of the mechanism of action of the active factor. Although the primary active substance appears to be a glycoprotein, secondary active factors are present which were not characterized. For example, there is residual inhibitory activity in the supernatant of the crude homogenate and in the material which is insoluble in NaOH.

These results suggest that a glycoprotein or proteoglycan normally present in normal brain tissue conveys regulatory signals to the immune system. On the basis of these results, one can postulate that regulatory signaling molecules are normally present in the brain and perhaps in other tissues. Recognition of these signals by the immune system should downregulate effector responses, and could function to turn off immune responses once infections have been eradicated or to prevent immune-mediated damage in normal intact tissues. These regulatory molecules should be located in the extracellular matrix or on the cell surface molecules where they would come in contact with leukocytes emigrating from blood vessels. Potential regulatory molecules include constituents of the extracellular matrix or cell surface molecules which leukocytes emigrating from blood vessels would be likely to contact. These molecules might be particularly susceptible to degradation by infectious organisms, thus permitting inflammatory responses when infection is present. This is consistent with the observed effects of the bacterially-derived neuraminidase on the suppressive activity.

Such a regulatory pathway might act in an analogous but opposite manner to the stimulatory pathways of the innate immune system. Several different typical bacterial products, such as lipopolysaccharide, N-formylated peptides, and bacterial DNA are recognized by receptors on cells of the innate immune system and stimulate immune function [16–18]. Conversely, recognition of typical self products by specific self-receptors on leukocytes could inhibit or regulate immune responses.

There is growing experimental evidence in support of this idea. Tenascin, an extracellular matrix protein, inhibits in vitro proliferation to soluble antigen, alloantigen, and ConA, but does not inhibit proliferation to IL-2, anti-CD3 antibody, or ionomycin/PMA [19]. These effects are similar, but not identical to our current results. The MUC1 mucin also inhibits T cell proliferation to alloantigen and anti-CD3 antibody, but this effect can be overcome by IL-2 [22]. In other systems, an intact microenvironment prevents autoimmune disease in transgenic mice [20], fibroblasts and other cells secrete factors which induce activated T cells to enter a quiescent state [21], and the glycans heparin, heparan sulfate, keratan sulfate, and hyaluronic acid have immunomodulatory properties [23–26]. The extracellular matrix can also bind cytokines and chemokines which can then interact with leukocytes [8].

The following references were cited herein:
1. Medawar, P. B., Immunity to homologous grafted skin. III. The fate of skin homografts transplanted to the brain, to subcutaneous tissue, and to the anterior chamber of the eye. British Journal of Experimental Pathology, 1948. 29: p. 58–69.
2. Barker, C. F. and R. E. Billingham, Immunologically privileged sites. Advances in Immunology, 1977. 25: p. 1–54.
3. Streilein, J. W., B. R. Ksander, and A. W. Taylor, Immune deviation in relation to ocular immune privilege. Journal of Immunology, 1997. 158: p. 3557–3560.
4. Griffith, T. S., et al., Fas ligand-induced apoptosis as a mechanism of immune privilege. Science, 1995. 270: p. 1189–1192.
5. Wilbanks, G. A. and J. W. Streilein, Fluids from immune privileged sites endow macrophages with the capacity to induce antigen-specific immune deviation via a mechanism involving transforming growth factor-beta. European Journal of Immunology, 1992. 22: p. 1031–1036.
6. Gordon, L. B., et al., Normal cerebrospinal fluid suppresses the in vitro development of cytotoxic T cells: Role of the brain microenvironment in CNS immune regulation. Journal of Neuroimmunology, 1998. 88: p. 77–84.
7. Irani, D. N., K. I. Lin, and D. E. Griffin, Brain-derived gangliosides regulate the cytokine production and proliferation of activated T cells. Journal of Immunology, 1996. 157: p. 4333–4340.
8. Gilat, D., et al., Interplay of T cells and cytokines in the context of enzymatically modified extracellular matrix. Immunology Today, 1996. 17: p. 16–20.
9. Ueno, K., S. Ando, and R. K. Yu, Gangliosides of human, cat, and rabbit spinal cords and cord myelin. Journal of Lipid Research, 1978. 19: p. 863–871.
10. Iwamori, M. and Y. Nagai, A new chromatographic approach to the resolution of individual gangliosides. Biochimica et Biophysica Acta, 1978. 528: p. 257–267.
11. Waki, H., et al., Facile methods for isolation and determination of gangliosides in a small scale: Age-related changes of gangliosides in mouse brain synaptic plasma membranes. Analytical Biochemistry, 1994. 222: p. 156–162.
12. Wolfe, L. S., Methods for separation and determination of gangliosides., in Research methods in Neurochemistry, N. Marks, Editor. 1972, Plenum Press: New York. p. 233–248.
13. Manzi, A. and J. Esko, Direct chemical analysis of glycoconjugates for carbohydrates., in Current Protocols in Molecular Biology, F. M. Ausubel, et al., Editors. 1995, John Wiley and Sons: New York. p. 17.9.1–17.9.11.
14. Labarca, C. and K. Paigen, A simple, rapid, and sensitive DNA assay procedure. Analytical Biochemistry, 1980. 102: p. 344–352.
15. Bradford, M. M., A rapid and sensitive method for the quantitation of microgram quantities of protein utilizing the principle of protein-dye binding. Analytical Biochemistry, 1976. 72: p. 248–254.
16. Janeway, C. A., Jr, The immune system evolved to discriminate infectious nonself from noninfectious self. Immunology Today, 1992. 13(1): p. 11–16.
17. Fearon, D. T. and R. M. Locksley, The instructive role of innate immunity in the acquired immune response. Science, 1996. 272: p. 50–54.
18. Medzhitov, R. and C. A. Janeway, Innate immunity: The virtues of a nonclonal system of recognition. Cell, 1997. 91: p. 295–298.
19. Ruegg, et al., Tenascin, an extracellular matrix protein, exerts immunomodulatory activities. Proceedings of the National Academy of Sciences of the United States of America, 1989. 86: p. 7437-7441.

20. Limmer, A., et al., Failure to induce organ-specific autoimmunity be breaking of tolerance: importance of the microenvironment. European Journal of Immunology, 1998. 28: p. 2395–2406.
21. Akbar, A. N. and M. Salmon, Cellular environments and apoptosis: tissue microenvironments control activated T-cell death. Immunology Today, 1997. 18: p. 72–76.
22. Agrawal, B., Krantz, M. J., Reddish, M. A. and Longenecker, M. B., Cancer-associated MUC1 mucin inhibits human T-cell proliferation, which is reversible by IL-2. Nature Med, 1998. 4:43–49.
23. Chevrier, A., Girard, N., Delpech, B. and Gilbert, D., Inhibition of active E rosette forming T lymphocytes by hyaluronic acid. Evidence of a receptor for hyaluronic acid on a lymphocyte subpopulation. Biomedicine, 1982. 36:100–103.
24. Gorski, A., Wasik, M., Nowaczyk, M. and Korczak-Kowalska, G., Immunomodulating activity of heparin. FASEB J., 1991. 5:2287–2291.
25. Wrenshall, L. E., Cerra, F. B., Carlson, A., Bach, F. H. and Platt, J. L., Regulation of murine splenocyte responses by heparan sulfate. J. Immunol., 1991. 147:455–459.
26. Funderburgh, J. L., Mitschler. R. R., Funderburgh, M. L., Roth, M. R., Chapes, S. K. and Conrad, G. W., Macrophage receptors for lumican. A corneal keratan sulfate proteoglycan. Invest. Ophthalmol. Vis. Sci., 1997. 38:1159–1167.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A mammalian brain homogenate containing an alkali soluble active factor which inhibits antigen-stimulated proliferation of lymphocytes in vitro, wherein said active factor sediments in a particulate complex at 14,000 g; is heat stable; is inactivated by digestion with trypsin, proteinase K or neuraminidase; is not inactivated by formalin treatment or digestion with hyaluronidase; and, can be partially purified by a method comprising the following steps:
   a) centrifuging the brain homogenate at 14,000 g,
   b) solubilizing the factor in 0.04 N NaOH,
   c) applying the resulting solubilized factor to a 6HR 10/30 sepharose gel filtration column equilibrated with 0.04 N NaOH, and
   d) eluting said factor from the column with 0.4 N NaOH.

2. The brain homogenate of claim 1, wherein said homogenate inhibits the proliferation of antigen-stimulated lymphocytes but enhances the proliferation of most mitogen-stimulated lymphocytes.

3. The brain homogenate of claim 1, wherein said homogenate inhibits lymphocyte proliferation resulting from stimulation with one or more of the antigens selected from the group consisting of chicken ovalbumin and the purified protein derivative of *Mycobacterium tuberculosis*.

4. The brain homogenate of claim 1, wherein said homogenate enhances lymphocyte proliferation resulting from stimulation with at least one of the mitogens selected from the group consisting of concanavalin A, lipopolysaccharide, and anti-CD3 antibody.

5. The brain homogenate of claim 1, wherein said homogenate inhibits lymphocyte proliferation resulting from mitogen stimulation with ionomycin with phorbol 12-myristate 13-acetate.

6. The brain homogenate of claim 1, wherein said active factor inhibits the stimulation of lymphocyte proliferation by blocking the effects of IL-2.

* * * * *

UNITED STATES PATENT AND TRADEMARK OFFICE
CERTIFICATE OF CORRECTION

PATENT NO.    : 6,352,723 B1
DATED         : March 5, 2002
INVENTOR(S)   : J. William Lindsey It is certified that error appears in the above-identified patent and that said Letters Patent is hereby corrected as shown below:

Column 1,
Line 62, please insert a period after the word "lymphocytes".

Column 2,
Line 7, please insert the word -- the -- between the words "of" and "activity".

Column 3,
Line 12, please delete the word "is".

Column 5,
Line 62, "25 $\mu$g/ml" should read -- 2.5 $\mu$g/ml --.

Column 13,
Line 4, "be" should read -- by --.

Signed and Sealed this

Fifth Day of November, 2002

Attest:

JAMES E. ROGAN
Attesting Officer    Director of the United States Patent and Trademark Office